(12) United States Patent
Nelson et al.

(10) Patent No.: US 10,494,627 B2
(45) Date of Patent: Dec. 3, 2019

(54) EXTRACTION OF MATERIALS FROM REGIONS OF INTEREST IN A SAMPLE

(71) Applicant: General Electric Company, Schenectady, NY (US)

(72) Inventors: John Richard Nelson, Clifton Park, NY (US); Wei Gao, Clifton Park, NY (US); Christopher Michael Puleo, Niskayuna, NY (US); Todd Frederick Miller, Mechanicville, NY (US); Christine Lynne Pitner, Niskayuna, NY (US); David Andrew Shoudy, Niskayuna, NY (US); Alex David Corwin, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 53 days.

(21) Appl. No.: 15/453,719

(22) Filed: Mar. 8, 2017

(65) Prior Publication Data

US 2017/0175105 A1    Jun. 22, 2017

Related U.S. Application Data

(62) Division of application No. 14/557,169, filed on Dec. 1, 2014, now Pat. No. 9,625,355.

(51) Int. Cl.
*G01N 1/00* (2006.01)
*C12N 15/10* (2006.01)
(Continued)

(52) U.S. Cl.
CPC ......... *C12N 15/1013* (2013.01); *B01L 3/502* (2013.01); *C12Q 1/6806* (2013.01);
(Continued)

(58) Field of Classification Search
CPC ....................................................... G01N 1/00
See application file for complete search history.

(56) References Cited

U.S. PATENT DOCUMENTS 5,665,582 A    9/1997   Kausch et al.
5,843,644 A   12/1998   Liotta et al.
(Continued)

FOREIGN PATENT DOCUMENTS

EP        2177271 A1    4/2010
WO    2012102779 A2    8/2012

OTHER PUBLICATIONS

Alberts et al., "Isolating Cells and Growing Them in Culture". Molecular Biology of the cell. 4th edition, pp. 469-478, 2002.
(Continued)

*Primary Examiner* — Jyoti Nagpaul
(74) *Attorney, Agent, or Firm* — Eversheds Sutherland (US) LLP

(57) ABSTRACT

A system for extracting material from a region of interest includes a fluid delivery base comprising an inlet channel and an outlet channel formed within the fluid delivery base, a gasket affixed to the fluid delivery base, wherein the gasket comprises at least one opening exposing an open end of the inlet channel and an open end of the outlet channel; a support comprising a sample-supporting surface facing the gasket and an opposing surface; and an alignment member coupled to the opposing surface in a fixed position and such that the support is positioned between the fluid delivery base and the alignment member, wherein one or both of the alignment member or the fluid delivery base are biased towards one another by a force (e.g., a magnet or spring force) and wherein the fluid delivery base is separable from
(Continued)

the support and configured to move along a plane of the sample-supporting surface to align with the alignment member.

18 Claims, 10 Drawing Sheets

(51) Int. Cl.
*G01N 1/10* (2006.01)
*G01N 1/02* (2006.01)
*B01L 3/00* (2006.01)
*C12Q 1/6806* (2018.01)
*G01N 1/40* (2006.01)

(52) U.S. Cl.
CPC .............. *G01N 1/02* (2013.01); *G01N 1/10* (2013.01); *G01N 1/40* (2013.01); *B01L 2200/025* (2013.01); *B01L 2200/0689* (2013.01); *B01L 2300/06* (2013.01); *B01L 2300/0654* (2013.01); *B01L 2300/0861* (2013.01); *G01N 2001/028* (2013.01); *G01N 2001/4038* (2013.01)

(56) References Cited

U.S. PATENT DOCUMENTS

| | | | |
|---|---|---|---|
| 6,218,126 B1 | 4/2001 | Yasuda et al. | |
| 6,594,432 B2* | 7/2003 | Chen | B01J 19/0046 385/127 |
| 6,707,038 B2 | 3/2004 | Ellson et al. | |
| 6,925,317 B1 | 8/2005 | Samuels et al. | |
| 8,597,715 B2 | 12/2013 | Emmert-Buck et al. | |
| 2002/0037269 A1 | 3/2002 | Liotta et al. | |
| 2002/0182718 A1 | 12/2002 | Malmquist | |
| 2004/0085443 A1 | 5/2004 | Kallioniemi et al. | |
| 2004/0101870 A1 | 5/2004 | Caubet et al. | |
| 2006/0166253 A1 | 7/2006 | Kononen et al. | |
| 2007/0183936 A1 | 8/2007 | Newsam et al. | |
| 2010/0050300 A1 | 2/2010 | Cope | |
| 2010/0076185 A1 | 3/2010 | Adey et al. | |
| 2010/0190177 A1 | 7/2010 | Emmert-Buck et al. | |
| 2010/0261176 A1 | 10/2010 | Mitragotri et al. | |
| 2010/0322826 A1 | 12/2010 | Locascio et al. | |
| 2011/0129863 A1 | 6/2011 | Shoemaker et al. | |
| 2011/0177518 A1 | 7/2011 | Kartalov et al. | |
| 2011/0190153 A1 | 8/2011 | Adey et al. | |
| 2011/0194749 A1 | 8/2011 | Morris | |
| 2011/0287951 A1 | 11/2011 | Emmert-Buck et al. | |
| 2013/0109024 A1 | 5/2013 | Rajagopalan et al. | |
| 2013/0209326 A1 | 8/2013 | Williams et al. | |
| 2013/0217144 A1 | 8/2013 | Rida | |
| 2014/0024052 A1 | 1/2014 | Dapprich et al. | |
| 2014/0171342 A1 | 6/2014 | Gale et al. | |

OTHER PUBLICATIONS

Karle et al., "Continuous microfluidic DNA extraction using phase-transfer magnetophoresis", The Royal Society of Chemistry, vol. No. 10, Issue No. 23, pp. 3284-3290, 2010.

"Pinpoint Slide DNA Isolation System", Zymos Product catalogue, Catalog No. D3001, Mar. 19, 2014.

International Search Report and Written Opinion issued in connection with corresponding PCT Application No. PCT/US2015/061541 dated Jan. 22, 2016.

* cited by examiner

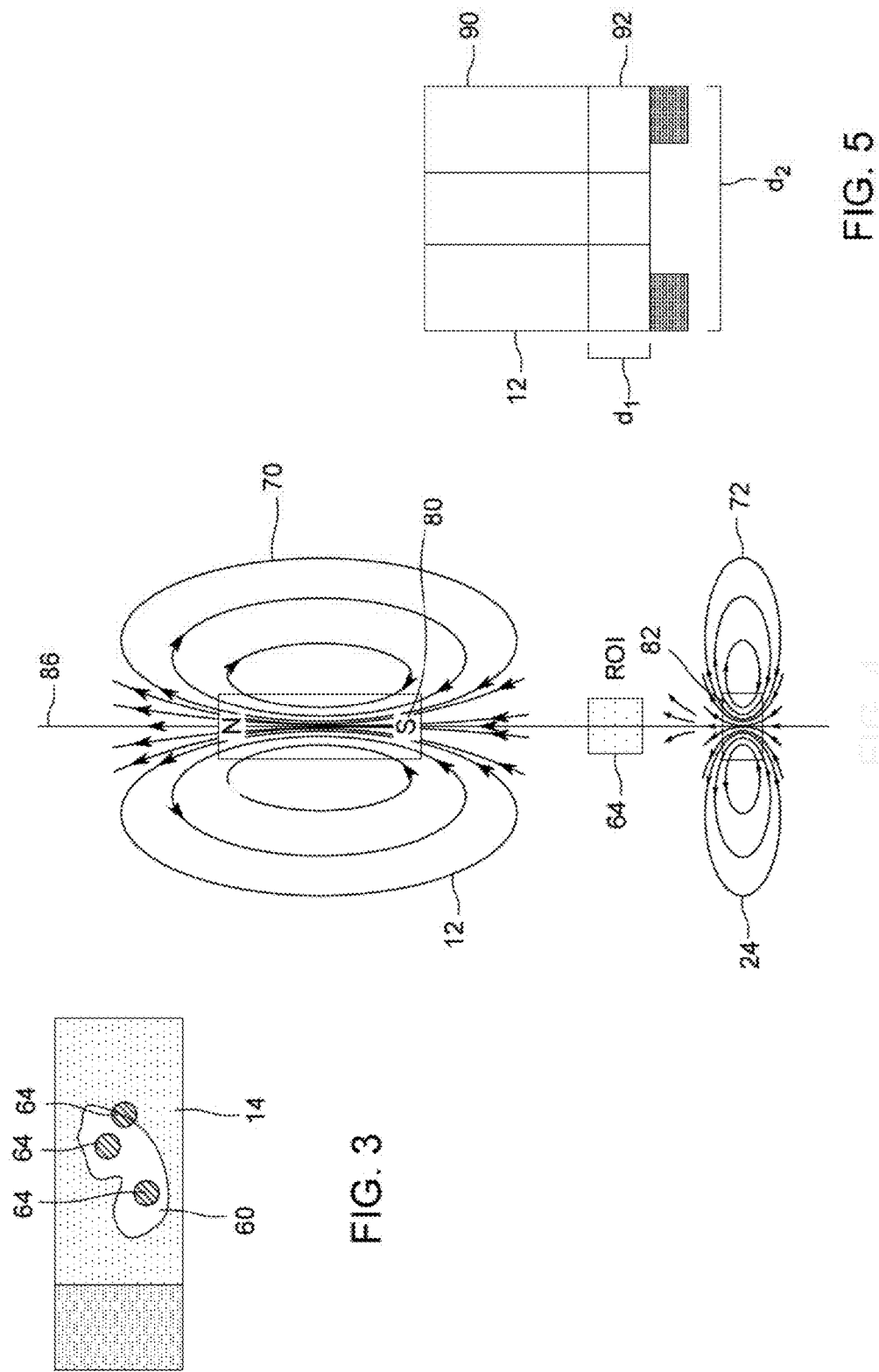

EXTRACTION OF MATERIALS FROM REGIONS OF INTEREST IN A SAMPLE

CROSS-REFERENCE TO RELATED APPLICATIONS

The present application is a divisional of U.S. patent application Ser. No. 14/557,169 entitled "EXTRACTION OF MATERIALS FROM REGIONS OF INTEREST IN A SAMPLE", filed Dec. 1, 2014, the disclosure of which is incorporated herein by reference in its entirety for all purposes.

BACKGROUND

The subject matter disclosed herein relates to techniques for extracting biological molecules from an existing sample, such as a pathology slide.

Medical researchers often obtain patient samples, such as biopsies, and preserve such samples as pathology slides, core samples, etc., for diagnosis and visualization. When such samples contain particular regions of interest, the researchers may wish to extract materials from these regions of interest for additional studies. For example, researchers may examine a slide including both tumor and normal cells, and may wish to extract DNA from only the tumor cells in the slide to assess the DNA for the presence of particular mutations. However, extraction of material from only a region of interest and without damaging the material is complex. For example, in laser capture micro-dissection, a focused laser beam ablates tissue to define a region of interest but damage the surrounding material. Other techniques may involve tissue encapsulation, which introduces an additional material to the sample.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a system for extracting material from a region of interest includes a fluid delivery base. The system also includes a first channel within the fluid delivery base and terminating at a first channel end at a sample-facing surface of the fluid delivery base, wherein the first channel comprises a first channel opening configured to couple to a fluid inlet to fluidically couple the fluid inlet the first channel end and a second channel within the fluid delivery base and terminating at a second channel end at the sample-facing surface of the fluid delivery base, wherein the second channel comprises a second channel opening configured to couple to fluid outlet to fluidically couple the fluid outlet to the second channel end. The system also includes a gasket coupled to the sample-facing surface and comprising a gasket opening aligned with an area of the sample-facing surface comprising the first channel end and the second channel end. The system also includes a support comprising a sample-supporting surface facing the gasket and an opposing surface and an alignment member coupled to the opposing surface, wherein the fluid delivery base is separable from the support and configured to move along a plane of the sample-supporting surface to align with the alignment member.

In another embodiment, a method of extracting material from a region of interest includes the steps of aligning one or more fluid channels of a fluid delivery base with an alignment member to define a region of interest on a sample, wherein the fluid delivery base and the alignment member are positioned on opposing surfaces of the sample such that the fluid delivery base and the alignment member are separated from one another by at least the sample and wherein the aligning comprises changing a position of the fluid delivery base or the alignment member relative to one another; delivering extraction fluid to the sample via the one or more fluid channels; and collecting the extraction fluid via the one or more fluid channels.

In yet another embodiment, a system for extracting material from a region of interest includes a fluid delivery base comprising one or more channels formed within the fluid delivery base, wherein the fluid delivery base comprises a metal; a gasket affixed to the fluid delivery base, wherein the gasket comprises at least one opening exposing an open end of at least one of the one or more channels; a support comprising a sample-supporting surface facing the gasket and an opposing surface; and an alignment member coupled to the opposing surface in a fixed position and such that the support is positioned between the fluid delivery base and the alignment member, wherein the fluid delivery base is separable from the support and configured to move along a plane of the sample-supporting surface to align with the alignment member.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 3 is a top view of an exemplary extraction system showing multiple regions of interest on the sample;

FIG. 4 is a schematic view of a magnetic field of a magnetic fluid delivery base and a magnetic alignment member in accordance with embodiments of the present techniques;

FIG. 5 is a cross-sectional view of a fluid delivery base in accordance with embodiments of the present techniques;

DETAILED DESCRIPTION

Figure 2:
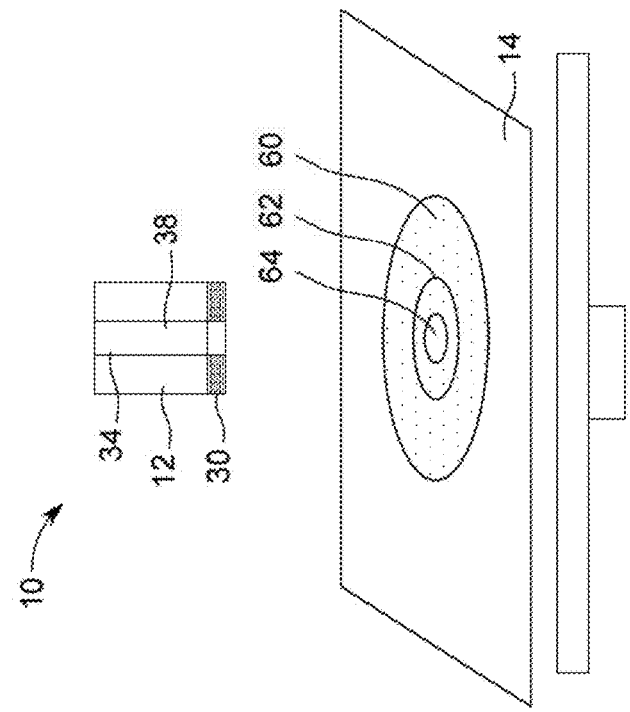
FIG. 2 is a partial cross-sectional view of the extraction system of FIG. 1 showing the isolation area on the sample.

Researchers may wish to extract regions of interest from biological or environmental samples with minimal disruption of the original slide or section. A region of interest may be any user-defined region on a sample, and may be a single cell, a subcellular region, or a multicellular region of a sample. Regardless of the region of interest for the user, techniques used for extracting regions of interest from the sample may damage the surrounding sample and/or may be expensive or complex. For example, laser-based techniques may be used that cut around a particular region of interest, but such techniques may involve expensive equipment, skilled technicians, and long processing times. For example, laser capture microdissection may involve complex associated sample preparation and is performed by skilled technicians Other techniques target a region of interest via transfer, such as applying liquid wax on a slide and removing the wax after solidification. However, such techniques are difficult to automate and provide only limited spatial resolution, in certain cases because the wax is difficult to limit to a particular location with high resolution. In another example, extraction may be achieved by physically scraping (and wasting) away all of the non-ROI tissue. Such physical extractions are associated with a destruction of the remaining sample, which prevents further analysis or sample mapping.

Provided herein is a self-aligning region of interest extraction technique that provides improved spatial resolution without complex equipment. In addition, the present techniques provide high extraction efficiencies for materials of interest within the sample, such as nucleic acids, without damaging the surrounding tissue. In turn, surrounding sample preservation allows for more complex analysis to be performed on a sample, such as mapping or heterogeneity analysis. The present techniques are also suitable for automation or higher throughput.

The disclosed techniques may be used in conjunction with samples of biological materials. As used herein, the term "biological material" refers to material obtained from samples of a biological subject, including biological tissue or fluid obtained from a subject. Such samples may be, but are not limited to, body fluid (e.g., blood, blood plasma, serum, or urine), tissues, fractions, and cells isolated from, or located in, any biological system, such as mammals. Biological samples and/or biological materials also may include sections of the biological sample including tissues (e.g., sectional portions of an organ or tissue). Biological samples may also include extracts from a biological sample, for example, a population of cells from a biological fluid (e.g., blood or urine). In certain embodiments, the biological material may include proteins, nucleic acids, carbohydrates, fatty acids, and/or small molecules. It should be understood that the samples may be histological samples, pathology samples, or tissue core samples and may be in the form of slides, sections, multi-well plates, etc. Further, the disclosed techniques may also be used in conjunction with non-biological samples, environmental samples, or forensic samples.

Figure 1:
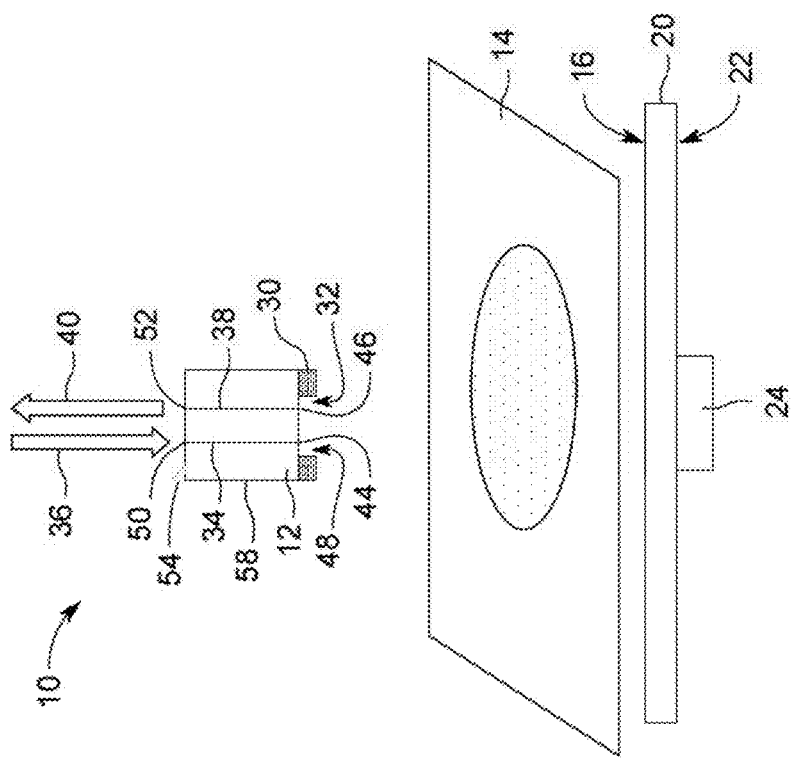
FIG. 1 is a partial cross-sectional view of an extraction system in accordance with embodiments of the present techniques.

Turning to FIG. 1, the extraction system 10 as provided herein includes a fluid delivery base 12 that, in operation, is positioned to deliver extraction fluid directly to the sample 14. The sample 12 is positioned on a top surface 16 of a support 20. A bottom surface 22 of the support 20 opposes the top surface and is coupled to or includes an alignment member 24. In operation, the fluid delivery base 12 is applied to the sample 14 by operator or machine manipulation. In one embodiment, the alignment member 24 and the fluid delivery base 12 self-align under magnetic force to hold the fluid delivery base 12 in position on the sample 14. In certain embodiments, one or both of the fluid delivery base 12 or the alignment member 24 is a magnet, e.g., a permanent magnet or an electromagnet. Such that the fluid delivery base 12 and the alignment member 24 magnetically align to hold the fluid delivery base 12 in place.

When the fluid delivery base 12 is aligned or correctly positioned on the sample 14, a gasket 30 on a sample-facing surface 32 of the fluid delivery base 12 comes into direct contact with the sample. Once a portion of the sample is isolated via the gasket 30, fluid delivery for extraction may take place. As depicted, the fluid delivery base 12 may include a fluid inlet channel 34 for delivering an extraction fluid, represented by arrow 36, to the isolated sample portion. Further, the fluid delivery base may include a fluid outlet channel 38 for collecting the incubated extraction liquid and recovered materials e.g., biological materials, represented by arrow 40.

The fluid delivery base 12 may include the channels 34 and 38 as integrally formed passageways within the body of the fluid delivery base 12. For example, the channels 34 and 38 may be formed via drilling or as part of an injection mold die. While the depicted embodiment includes a single inlet channel 34 and outlet channel 38, it should be understood that there may be any suitable number of channels 34 and 38, and that the channels 34 and 38 may be present in equal or unequal numbers. Further, the size (e.g., inner diameter) of each channel 34 or 38 may be selected based on a desired region of interest size. That is, for relatively small regions of interest, the channels 34 and 38 may be formed with correspondingly small inner diameters. In certain embodiments, the inlet and outlet functions may be achieved via a single channel used for inflow and outflow. Further, while the channels 34 and 38 may be formed within the fluid delivery base, in other embodiments, the fluid delivery base 12 may form a central passage (e.g. may be donut-shaped) that facilitates insertion of preformed channels 34 and 38 within the passageway. Such an embodiment may help keep the the fluid delivery base 12 isolated from contact with biological materials, which may in turn facilitate reuse.

The inlet channel 34 terminates at channel end 44 and the outlet channel 38 terminates at channel end 46 on the sample-facing surface 32 and within an area 48 defined by the gasket 30. In the depicted embodiment, the channels 34 and 38 are substantially parallel to one another and open at respective channel ends 50 and 52 disposed on a top surface 54 of the fluid delivery base 12. However, in other embodiments, the channels 34 and 38 may open on a side surface 58 and/or open at a specialized junction to accommodate couplings to upstream or downstream tubing. Further, the inlet and outlets channels 34 and 38 may be angled or nonparallel depending on the desired configuration of the fluid delivery base 12.

The fluid delivery base 12, in certain embodiments, is held in place on the sample 14 via magnetic force. FIG. 2 is a partial cross-sectional view of the system 10 showing a region of interest that may be isolated by the fluid delivery base 12. In operation, the gasket 30 makes direct contact with the sample material 60 at a contact area 62 to isolate a region of interest 64. When the gasket 30 makes direct contact, the extraction fluid from the inlet channel 34 is sealed from lateral diffusion across the sample material 60, which facilitates targeted extraction and recovery of the extracted material via outlet channel 38. Further, because the force on the sample 14 is a combination of the gasket sealing force and the magnetic pull force, the applied force may be selected to minimize pressure of the gasket on the sample material 60. To that end, the gasket may be formed from a relatively compliant sealing material, such as a compressible polymer. In particular embodiments, the gasket 30 may be hydrophobic to discourage any lateral diffusion of extraction fluid.

The fluid delivery base 12 and, in particular, the channels 34 and 38 may be configured based on a desired spatial resolution of the region of interest 64. In certain embodiments, the region of interest 64 may be less than or larger than 1 mm$^2$ or may be on the order of 100 microns or less. In other embodiments, the region of interest 64 may several centimeters square. Further, the region of interest may have any desired shape, including a circle, square, etc. The gasket 30 may be cut to an opening that defines the desired region of interest size and shape. In one embodiment, the gasket 30 may be cut to an opening that is defined by the system 10. For example, the system 10 may include imaging software under processor control. The user may view the sample 14 via a user interface and may define the region of interest 64 by providing inputs on the user interface, which may be viewed as a superimposed region on the sample image. Further, the gasket 30 may be selected based on the region of interest 64 or may be custom cut.

FIG. 3 is an example of a sample 14 showing region of interests that may be isolated by the fluid delivery base as provided herein. In certain embodiments, the system 10 provides for regions of interest 64 that encompass an edge or border of the sample material 60. For example, a clinician may wish to determine if cells on a border region have different characteristics than cells in the interior of the sample. The fluid delivery base is capable of isolating and sealing cells within the region of interest 64 even if the region of interest includes an edge, which provides advantages over other techniques that may not be able to isolate edge material. Further, the disclosed techniques may be used with poor quality samples that were either prepared poorly and/or that have degraded.

FIG. 4 is a schematic diagram of an embodiment in which both the fluid delivery base 12 and the alignment member 24 are magnets with a magnetic field (e.g., magnetic fields 70 and 72). For example, the fluid delivery base 12 is a bar magnet with a south pole 80 oriented towards the region of interest. The alignment member 24 may be oriented so that its north pole 82 is closest to the south pole 80 of the field delivery base 12 so that the fluid delivery base 12 and the alignment member 24 will attract one another as they are positioned closer together (by movement of one or both of the fluid delivery base 12 or the alignment member 24) to hold the fluid delivery base 12 on the region of interest 64. As shown, the alignment may occur along an axis 86 through the alignment member 24, the region of interest 64, and the fluid delivery base 12. Generally, the magnetic field 70 may extend beyond the region of interest 64 and towards the alignment member 24 when the fluid delivery base 12, via the gasket 30, is in direct contact with the sample 14. In addition, in such a configuration, the magnetic field of the alignment member 24 may extend beyond the region of interest 64 and towards the fluid delivery base 12.

It is contemplated that, in embodiments of the present techniques, both the fluid delivery base 12 and the alignment member 24 are magnets. However, in other embodiments, only one of the fluid delivery base 12 or the alignment member 24 is a magnet while the other is formed of or includes a ferrous material. Further, the fluid delivery base 12 or the alignment member 24 may be a permanent magnet, including iron, nickel, cobalt, a rare earth metal magnet, lodestone, a magnetic composite formed from a metallic magnetic material and a ceramic material or resin, a nanomagnet, etc. The fluid delivery base 12 or the alignment member 24 may also include an electromagnet.

FIG. 5 illustrates a cross-section of an implementation of a fluid delivery base 12 that may include a non-metallic or non-magnetic portion 90 and a metallic portion 92. In a particular embodiment, the metallic portion 92 may be magnetic. In the depicted embodiment, the metallic portion 92 is positioned towards the sample end of the fluid delivery base 12, (i.e., in contact with the gasket 30), but in other embodiments, the metallic portion 92 may form an exterior cylinder or casing for the fluid delivery base 12 while the core portion, including the fluid channels, may be formed of a non-metallic or non-ferrous material.

The configuration of the fluid delivery base 12 and the alignment member 24 (see FIG. 2) may be selected to achieve sufficient pull force to hold the fluid delivery base 12 without applying so much pressure as to damage the underlying sample when in operation. The magnet pull force may be influenced by the materials of the fluid delivery base 12 and the alignment member 24 (i.e., the magnet strength of certain materials is higher than other materials), and the size of the magnetic material. For example, the height (represented by d1) and width (represented by d2) as well as the depth of the fluid delivery base 12 or the alignment member 24 may influence the pull force. In one embodiment, the pull force, case 1, of the fluid delivery base, is less than 1 lb., e.g., between about 0.32 lb-0.8 lb. However, it should be understood that the pull force is related to the size of the magnet, and larger magnets may have larger pull forces. In one embodiment, a ring magnet having an inner diameter of about 0.06 inches and an outer diameter of about 0.2 inches and a height dimension of about 0.2 inches has a pull force, case 1, of about 0.32 lbs, a pull force, case 2, of about 0.38 lbs, and a pull force, case 3, of about 0.63 lbs may be used. A ring magnet having an inner diameter of about 0.125 inches and an outer diameter of about 0.25 inches and a height dimension of about 0.25 inches has a pull force, case 1, of about 0.64 lbs, a pull force, case 2, of about 0.80 lbs, and a pull force, case 3, of about 1.13 lbs may be used. In another embodiment, the pull force, case 1, is such that an operator may easily manually manipulate the fluid delivery base 12 relative to the sample 14 during removal or application. In the disclosed embodiments, the case 1 pull force is the pull force to remove a magnet from a steel plate, the case 2 pull force is the pull force to remove a first steel plate from a magnet with a second steel plate on an opposing face, and case 3 is the pull force to remove one magnet from another magnet.

In the depicted embodiment, the fluid delivery base 12 may include a mix of materials to form a shape that is sufficiently-sized to be gripped by an operator but is not so magnetically strong as to damage the underlying sample. That is, by mixing in materials that are relatively lightweight and nonmetallic, the fluid delivery base 12 may be made larger without being too heavy or without too strong of a magnetic field.

Figure 6:
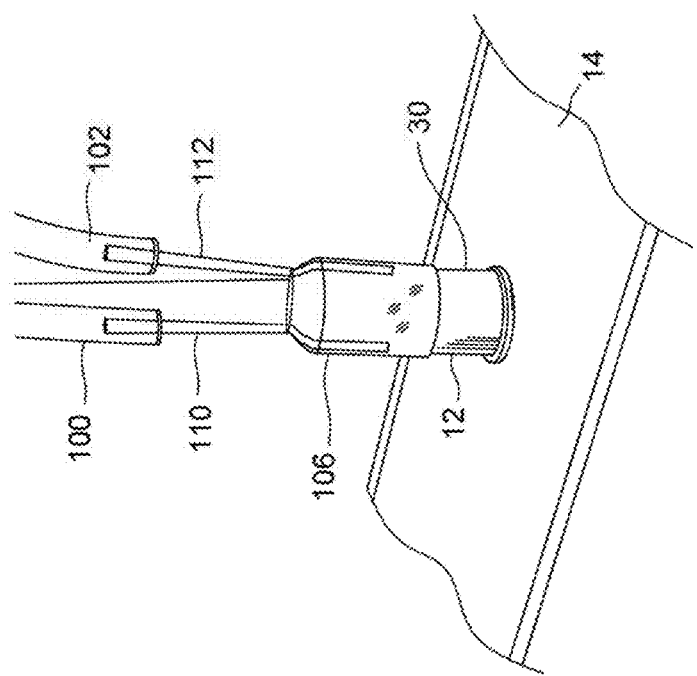
FIG. 6 is a perspective view of an extraction system in contact with a sample in accordance with embodiments of the present techniques.

FIG. 6 is an example of an implementation of the system 10, including the fluid delivery base 12 in place on a sample 14. The fluid delivery base is coupled to inflow tubing 100 and outflow tubing 102 via an adaptor 106. The adaptor 106 may include interior channels that couple to the inlet and outlet channels 34 and 38 within the fluid delivery base and exterior channels 110 and 112 to couple to the inflow tubing 100 and outflow tubing 102. It is contemplated that all or part of the portion of the system 10 above the sample 14 (e.g., in contact with the sample 14) may be disposable. For example, in one embodiment, the gasket 30 may be removable from the fluid delivery base 12, which may be cleaned and retained for additional uses while the gasket 30 is discarded. In addition, the adaptor 106 and the tubing 100 and 102 may be provided as a disposable attachment to the fluid delivery base. Alternatively, the fluid delivery base 12 may be assembled as a unitary assembly with the gasket 30 and the adaptor 106 fixed in place on (e.g. bonded or adhered to) the fluid delivery base 12. In another embodiment, the tubing may couple directly to the fluid delivery base 12 without an adaptor 106 or fluid reservoir. Accordingly, in one embodiment, a sample extraction kit may include a fluid delivery base 12 with a gasket 30 and an adaptor 106 in place on the fluid delivery base 12. The kit may, in certain embodiments, also include sections of tubing that may be attached, whether during assembly or by an end user, to the exterior channels 110 and 112 to form inflow tubing 100 and outflow tubing 102.

Further, in particular embodiments, such a kit may also include one or more materials for performing an extraction from a sample 14. For example, if the sample is a paraffin-embedded tissue section on a glass slide, the kit may include proteinase K for nucleic acid extraction. In one embodiment, an adaptor may be packed with a suitable amount of proteinase K to apply to the sample 14 via the fluid delivery base 12. The kit may also include a selection of gaskets 30 with different opening sizes that facilitate extraction of different-sized regions of interest. An operator may select a gasket 30 with an opening corresponding to the desired region of interest size and apply the gasket 30 prior to the extraction. The gaskets 30 may be removable/replaceable, and may be peeled away and discarded after use.

Figure 7:
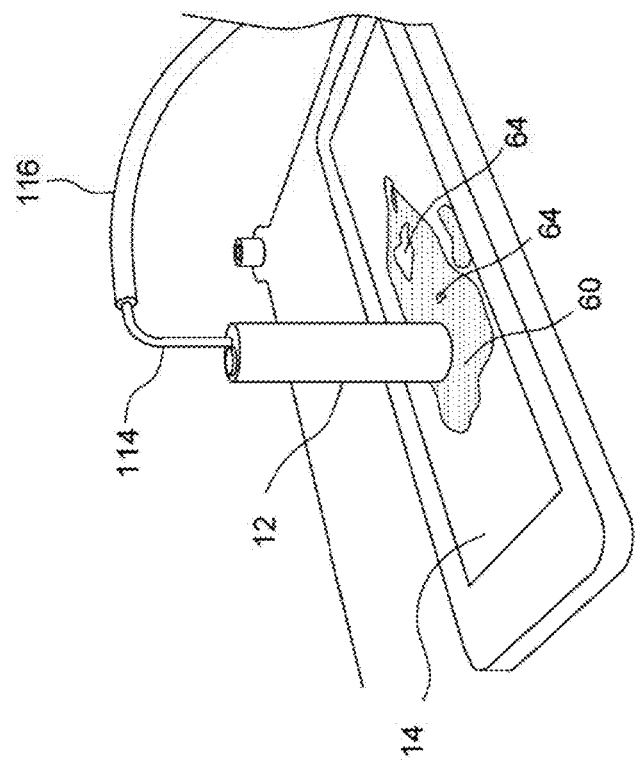
FIG. 7 is a perspective view of an alternative extraction system in contact with a sample in accordance with embodiments of the present techniques.

FIG. 7 is an example of an implementation of the fluid delivery base 12 in place on a sample 14 in which a single channel is used for the outlet channels within the fluid delivery base. A coupler including the outlet 114 is fluidically coupled to tubing 116. The sample may be loaded into an integral reservoir in the fluid delivery base 12. In operation, the user loads the buffer into the reservoir, which is then pulled to the sample 14. In addition, the sample 14 is shown with sample material 60 having already been isolated from a region of interest 64 (shown as having the sample material removed in a complete circle) and in place on a second region of interest.

In the various embodiments of the system disclosed herein, the isolation and extraction of material from a particular region of interest 64 may be performed in conjunction with enzyme or chemical delivery to the region of interest 64, e.g., via inlet channel 34 or the coupler 114 to facilitate liquefication of the sample material 60 and subsequent extraction. By performing the extraction on a region of limited size, the extraction workflow may be improved. For example, depending on the enzyme delivered to the region of interest and the temperature of the sample 14, the incubation time may be on the order of seconds (e.g., less than 10 seconds) rather than several minutes as in other techniques. In particular, more rapid extraction times may be achieved by agitating the fluid including a buffer and enzyme. Increased temperature may also reduce extraction times. However, longer incubation times are also contemplated. Any suitable extraction enzyme may be used, such as proteinase K. In other embodiments, the fluid delivery base 12 may be used for liquefication and extraction that is not chemically or enzymatically mediated.

Figure 8:
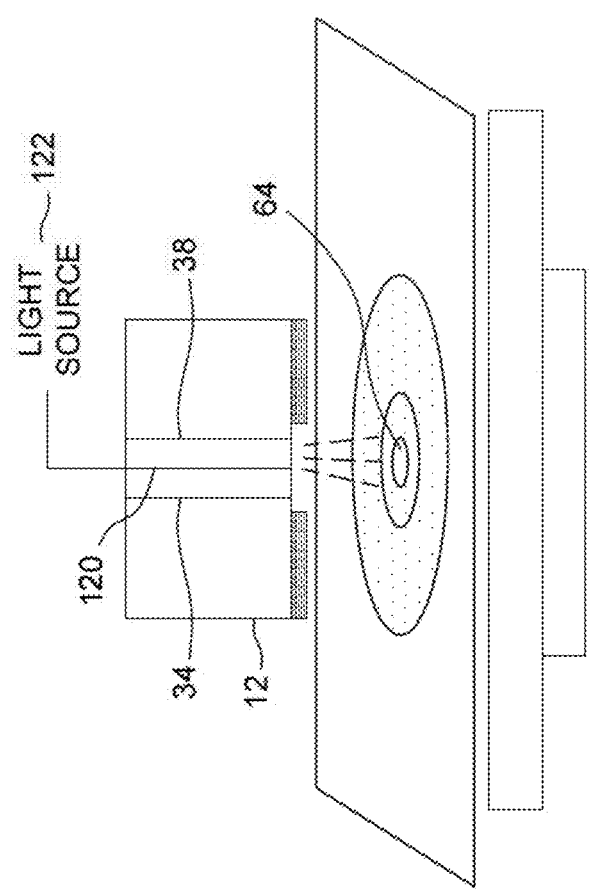
FIG. 8 is a partial cross-sectional view of an extraction system including an internal light in accordance with embodiments of the present techniques.

FIG. 8 illustrates a cross-section of an implementation of a fluid delivery base 12 that may include a light source. In operation, as the base 12 moves towards the sample, the emitted light from the light source may help identify the region of interest 64 to assist in proper placement of the fluid delivery base 12 and subsequent material extraction from the sample. For example, the fluid delivery base 12 may include one or more dedicated light channels 120 coupled to a light source 122 (e.g., an LED), which may be on or in the fluid delivery base 12 or may be external to the base 12. Optical fibers may be disposed in the one or more light channels 120, or the channel 120 itself may form a light pipe. Such an arrangement may be advantageous because the relatively small footprint of an optical fiber or light pipe may help the spatial resolution of the region of interest 64, e.g., for regions of interest that are less than 1 $mm_2$. However, in cases where the region of interest is larger, the light source may be directly disposed on or in the sample-contacting surface 32 (see FIG. 1) fluid delivery base 12.

Figure 9:
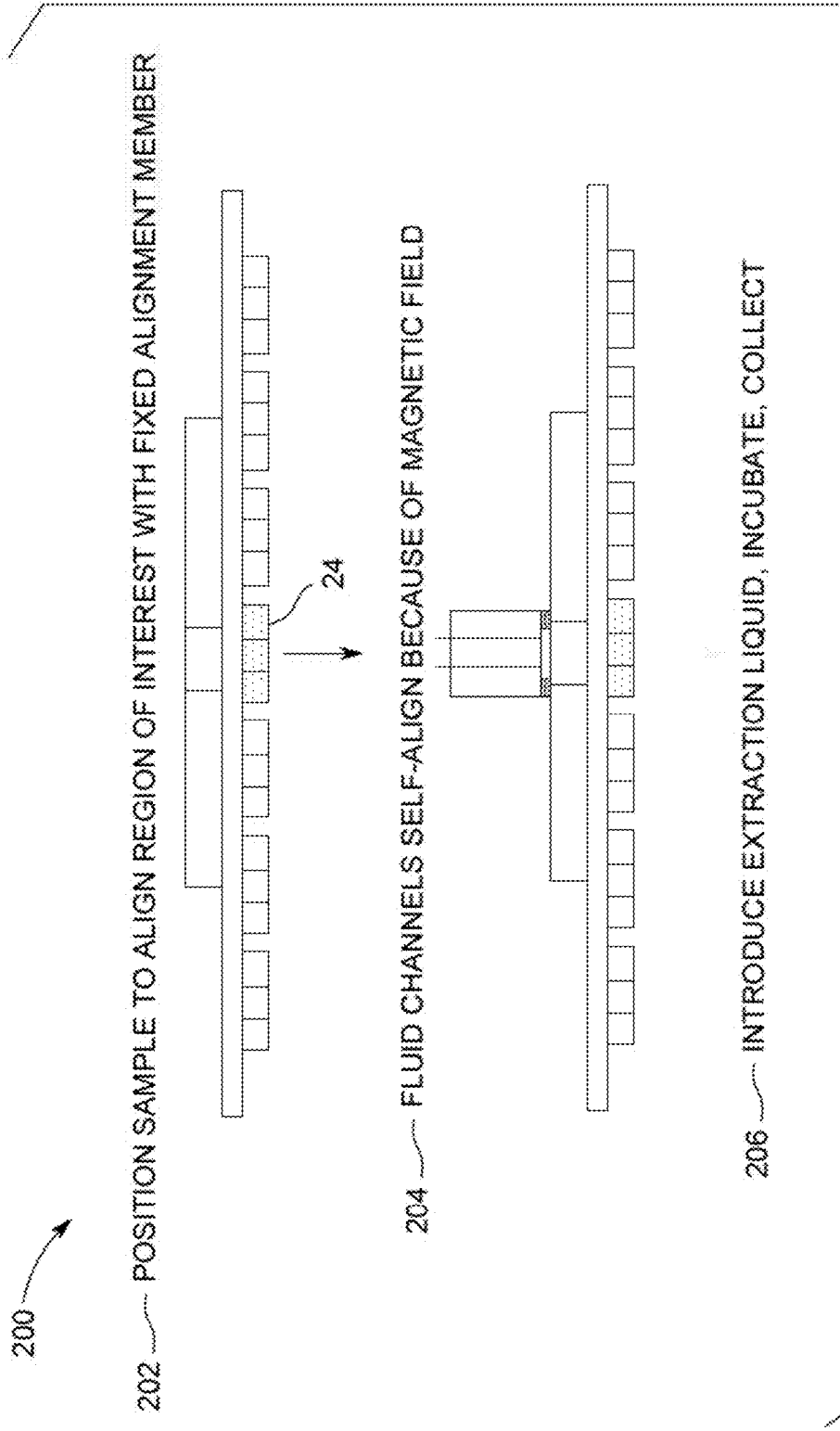
FIG. 9 is a schematic representation of a technique for aligning the separable fluid delivery base of an extraction system with a fixed alignment member in accordance with embodiments of the present techniques.

The fluid delivery base 12 as provided herein may be used in conjunction with a fixed or separable alignment member 24. FIG. 9 is a schematic flow diagram of a technique 200 for using the system 10 with the alignment member 24 fixed in place on (e.g., integral with, adhered to, or part of) the support 20. For example, in certain embodiments, it may be more convenient and provide more uniform results to have the alignment member 24 fixed in place on the support 20 or sample platform. At step 202, the operator positions the sample 14 on the support 20 at a sample placement location such that the region of interest 64 corresponds with a location of the alignment member 24 on the opposing surface 22. In such embodiments, the support 20 may include an indicator or marking that indicates the sample placement location. At step 204, the fluid delivery base 12 is applied to sample 14 to isolate the region of interest 64 and the alignment member 24 and the fluid delivery base 12 self-align (e.g., the alignment is supported by the strength of the magnetic attraction between these components). Once aligned, the extraction liquid may be introduced at step 206 for incubation and collection of materials extracted from the region of interest.

Figure 10:
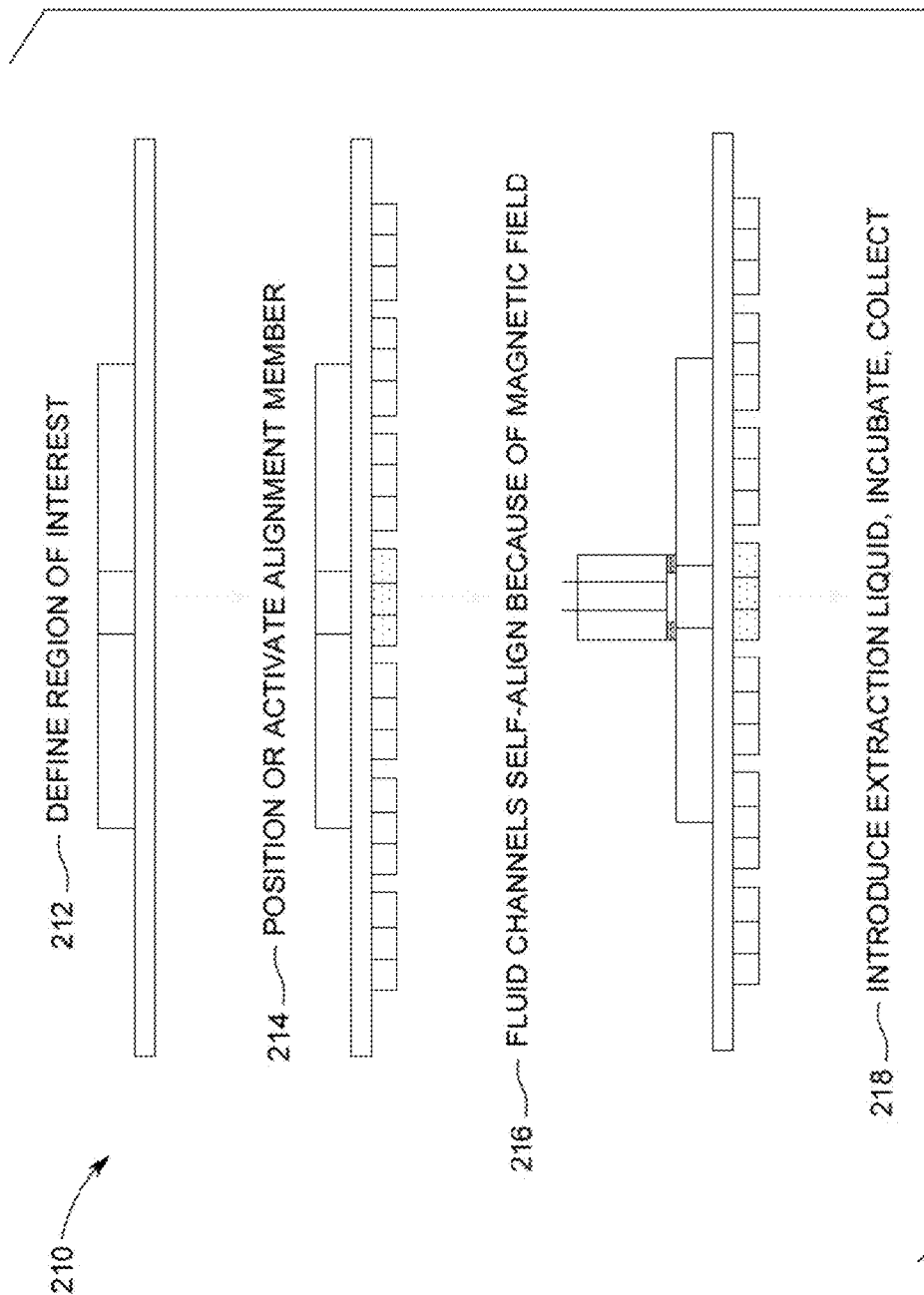
FIG. 10 is a schematic representation of a technique for aligning the separable fluid delivery base of an extraction system with a removable alignment member in accordance with embodiments of the present techniques.

FIG. 10 is a schematic flow diagram of an alternate technique 210 for using the system 10 with a movable alignment member 24. At step 212, the operator positions the sample 14 on the support 20. At step 214, the operator either positions the alignment member 24 on the opposing surface 22 or, alternatively, activates an alignment member that is fixed in place. In one embodiment, the system 10 may include multiple alignment members 24 but may only activate (e.g., apply current to activate an electromagnet) one of the set. Accordingly, the sample placement location would correspond to the active alignment member. Such an embodiment may permit relatively small alignment members 24 to be used to improve spatial resolution. Once aligned at step 216, the extraction liquid may be introduced at step 218 for incubation and collection of materials extracted from the region of interest.

Figure 11:
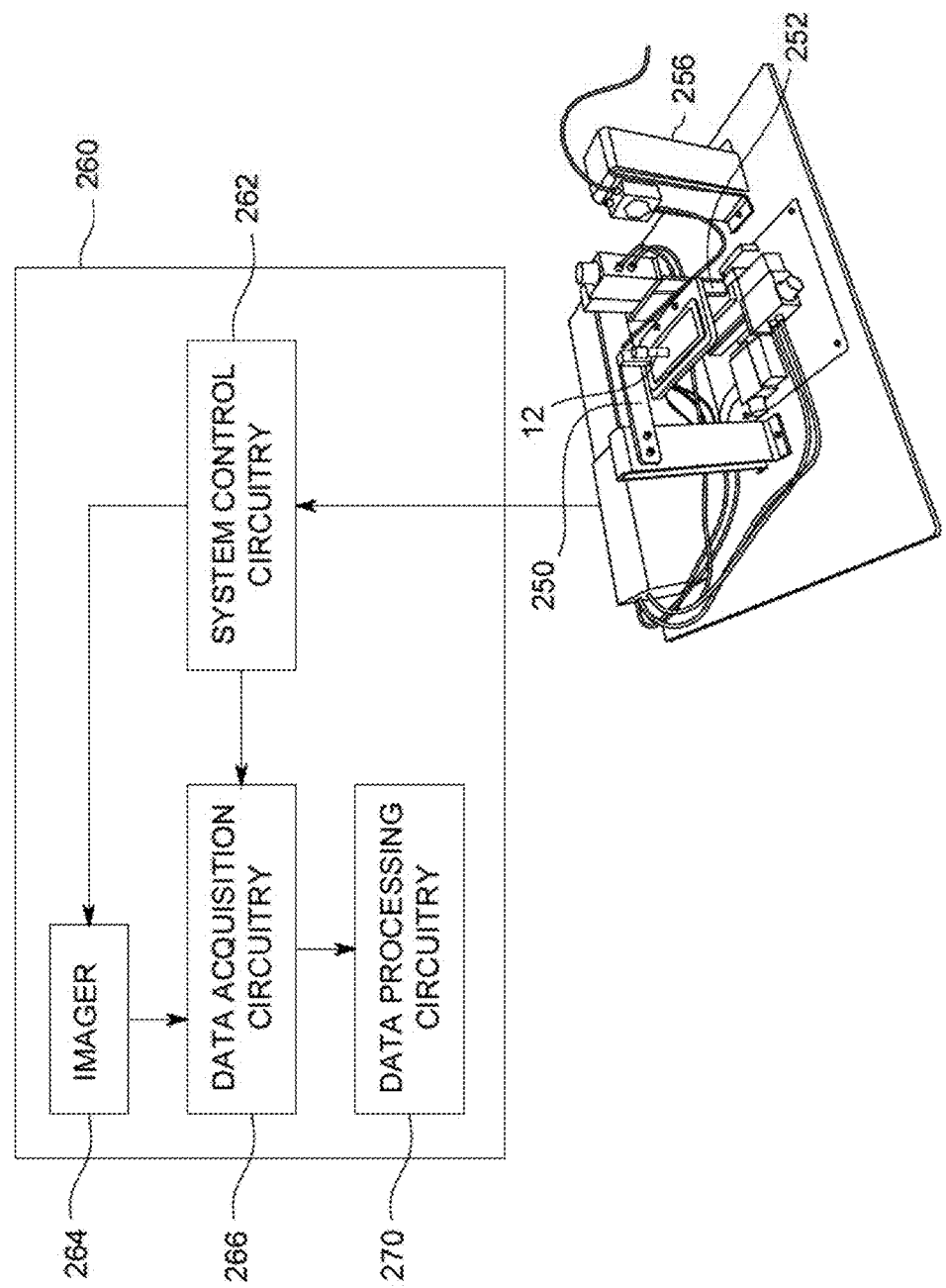
FIG. 11 is a side view of an extraction system including an adjustable arm in accordance with embodiments of the present techniques.

While the fluid delivery base 12 and/or the alignment member 24 may be positioned manually, the system 10 may also be used in conjunction with a mechanical manipulator. For example, FIG. 11 is a side view of an extraction device 256 that includes a mechanical arm 250 and coupled to a base holder 252 that holds the fluid delivery base 12. The base holder 252 changes position relative to the mechanical arm 250 (either by moving or by staying in place when the mechanical arm 250 is moved) to position the fluid delivery base 12 in close proximity to and on the sample 14. Further, while certain embodiments, of the disclosed techniques relate to magnetic alignment of the fluid delivery base on the sample, the fluid delivery base 12 may also be held in place with other biasing forces, e.g., spring force.

The extraction device 256 may also be coupled to a controller 260 that facilitates image analysis of the sample (e.g., sample 14) and movement/alignment of the fluid delivery base at a selected region of interest. Accordingly, the extraction device 256 may include an imager 264 that detects signals and converts the signals to data that may be processed by downstream processors. The imager 264 may operate in accordance with various physical principles for creating the image data and may include a fluorescent microscope, a bright field microscope, or devices adapted for suitable imaging modalities. In general, however, the imager 264 creates image data indicative of the sample 14

The imager 264 and/or the extraction device 256 and mechanical arm 250 operate under the control of system control circuitry 262. The system control circuitry 262 may include a wide range of circuits, such as illumination source control circuits, timing circuits, circuits for coordinating data acquisition in conjunction with sample movements, circuits for controlling the position of light sources and detectors and the fluid delivery base 12, and so forth. In the present context, the system control circuitry 262 may also include computer-readable memory elements, such as magnetic, electronic, or optical storage media, for storing programs and routines executed by the system control circuitry 262 or by associated components of the system 10. The stored programs or routines may include programs or routines for performing all or part of the present technique.

Image data acquired by the imager 256 may be processed by the imager 12, for a variety of purposes, for example to convert the acquired data or signal to digital values, and provided to data acquisition circuitry 266. The data acquisition circuitry 266 may perform a wide range of processing functions, such as adjustment of digital dynamic ranges, smoothing or sharpening of data, as well as compiling of data streams and files, where desired. The data acquisition circuitry 266 may also transfer acquired image data to data processing circuitry 270 where additional processing and analysis may be performed. The controller 260 may include one or more processor-based components, such as general purpose or application-specific computers. In addition to the processor-based components, the computer may include various memory and/or storage components including magnetic and optical mass storage devices and/or internal memory, such as RAM chips. The memory and/or storage components may be used for storing programs and routines for performing the techniques described herein that are executed by the operator workstation or by associated components of the system 10. Alternatively, the programs and routines may be stored on a computer accessible storage medium and/or memory remote from the operator workstation but accessible by network and/or communication interfaces present on the computer. In one embodiment, the controller 260 may facilitate operator selection of a region of interest 64 (e.g., via a user interface) on an image of the sample 14 acquired by the image 264 and displayed via the user interface. The controller 260 may also control movement of the fluid delivery base 12 via the mechanical arm 250 to position the fluid delivery base 12 on the region of interest 64. The controller 260 may also control fluid inflow and outflow, and may include one or more settings for controlling flow rate and/or incubation time.

Figure 12:
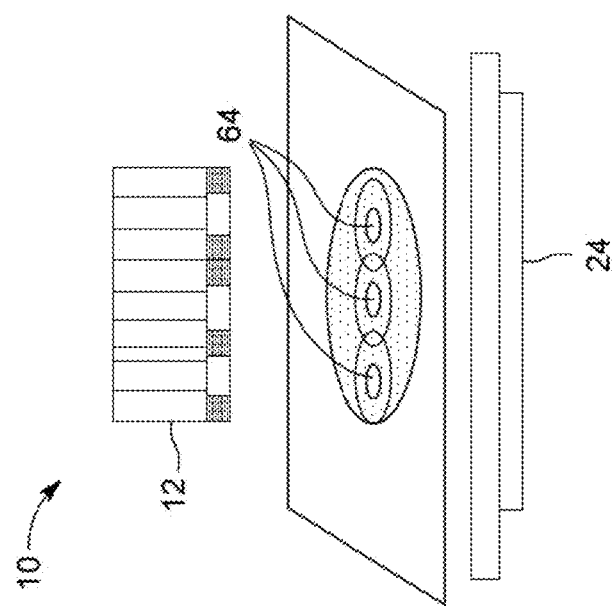
FIG. 12 a partial cross-sectional view of a multi-region of interest extraction system in accordance with embodiments of the present techniques.
Figure 13:
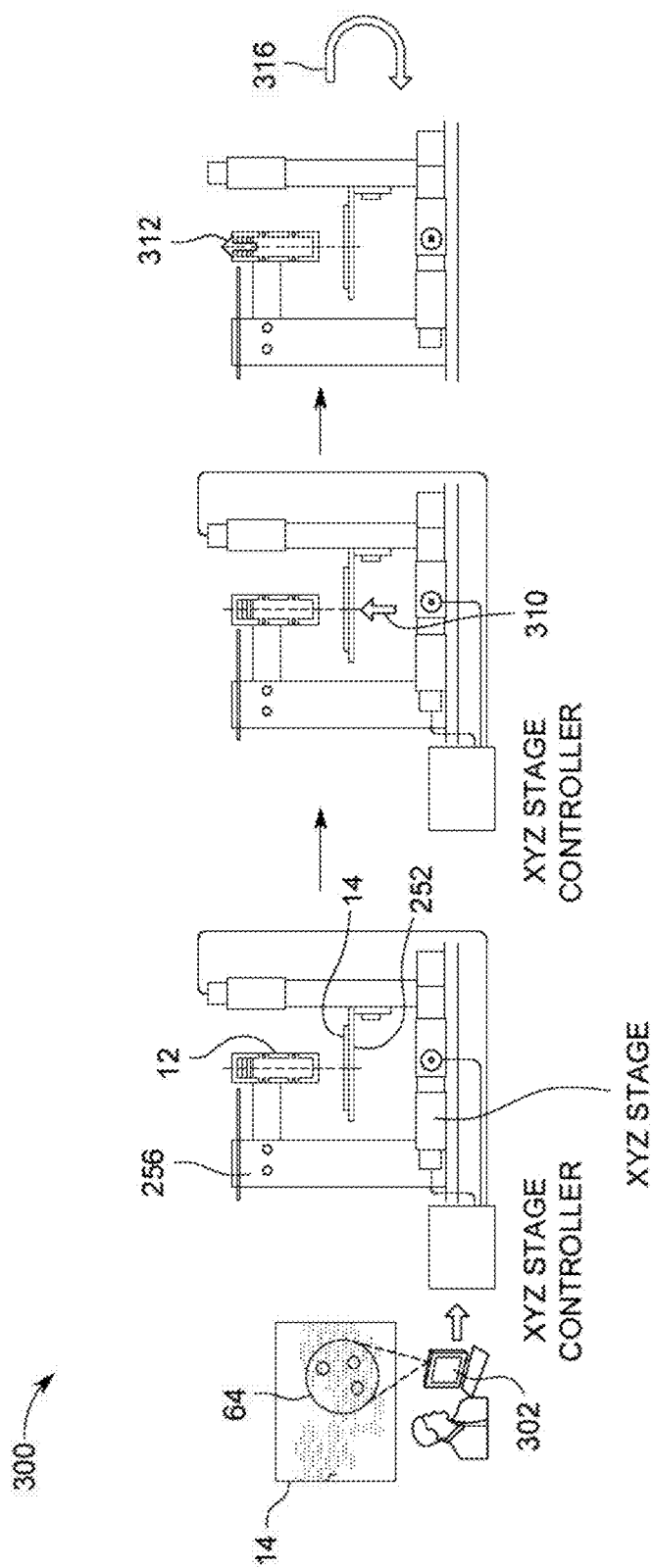
FIG. 13 is a schematic representation of a technique for aligning the fluid delivery base of a fluid extraction device with a sample on an x-y-z stage in accordance with embodiments of the present techniques.

The extraction techniques disclosed herein may also be used in parallel, as shown in FIG. 12, which illustrates a fluid delivery base 12 capable of isolating multiple regions of interest 64 in parallel. Such a configuration may be used for sample mapping, and the system 10 may extract biological materials from multiple locations on a sample slide for further analysis. Accordingly, in certain embodiments, the controller 260 (FIG. 11) may be used to define multiple regions of interest. Alternatively, the positioning may occur manually. FIG. 13 is a schematic view of a technique 300 for manipulating the fluid delivery base 12 relative to the sample 14 using the fluid extraction device 256. The operator views selects or view automatically selected regions of interest superimposed on an acquired image on a workstation 302, which may be coupled to the controller 260 (see FIG. 11). The operator may provide inputs to select or confirm the regions of interest, which activates movement of a stage holding the sample 14, the fluid delivery base 12, or both as indicated by arrow 310 to correctly align the fluid delivery base 12 on the region/s of interest. The stage may be an x-y-z stage with freedom of movement in the x, y, and z directions. Further, the fluid delivery base 12 may also include an actuator or stage in the x, y, and/or z direction. In the case of multiple regions of interest 64, the fluid delivery base may be positioned concurrently on all of them (with associated separate isolation gaskets 30), or may be operated to align with each in series. Fluid extraction, represented by arrow 312, occurs once the fluid delivery base 12 is positioned in place. The alignment may occur via an imaging or registration step in which the coordinates of the region of interest 64 are acquired during imaging and the fluid extraction device is controlled to position the fluid delivery base 12 at the appropriate coordinates.

Selection of the regions of interest 64 may be coupled to the image acquisition. For example, the sample 14 may be stained with one or more stains specific for biological markers. The regions of interest 64 may include the regions that are positive for the biological markers. The controller 260 may be configured to align the fluid delivery base 12 with the areas of the sample 14 positive for biological markers of interest. In this manner, biomolecules, cells, and/or regions expressing specific proteins or markers may be extracted from the sample 14 for further analysis. In one embodiment, an operator may select the biomarker of interest via the workstation 302 and the controller 260 may automatically extract regions including the biomarker.

The following is an example of an extraction performed with an extraction system, such as the systems disclosed herein. For region of interest extractions on colon tissue, the extraction diameter was 2 mm. Table 1 shows the extraction results:

TABLE 1

Extraction of Colon Tissue

|  | Sample 1 | Sample 2 | Sample 3 | Sample 4 |
|---|---|---|---|---|
| DNA (ng/uL) | 6.70 | 6.82 | 7.70 | 9.13 |
| Total DNA Yield (ng) | 36.83 | 34.08 | 42.37 | 43.83 |
| DNA (ng)/mm^2) | 11.73 | 10.86 | 13.49 | 13.96 |

Figure 14:
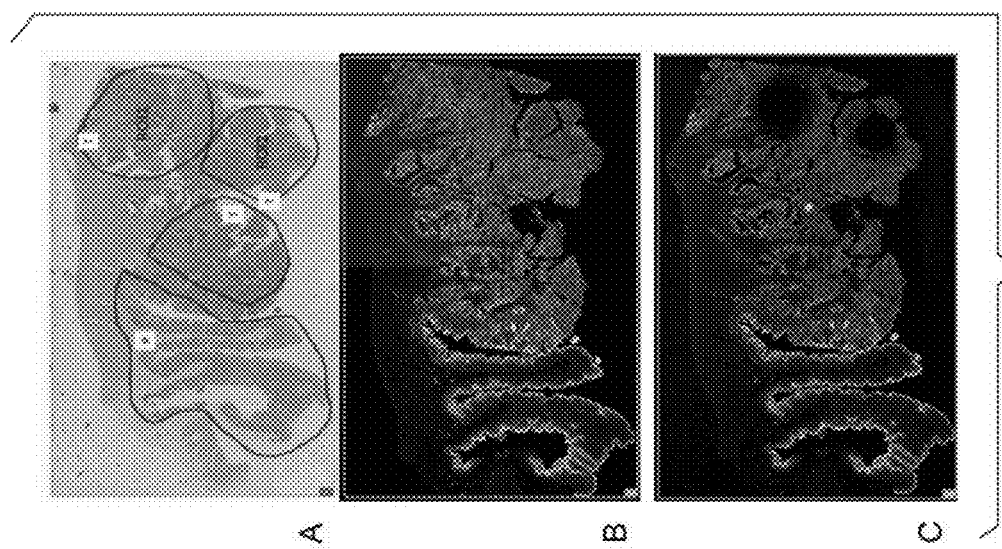
FIG. 14 is a stained image of a colon adenocarcinoma with the top panel showing DNA staining and including background, the middle panel showing staining with the background removed and the bottom panel after region of extraction removal.

The following is an example of an extraction performed with an extraction system, such as the systems disclosed herein. FIG. 14 shows images before and after extraction. Table 2 shows the extraction results:

TABLE 2

Extraction of Colon Adenocarcinoma

|  | Sample 1 | Sample 2 |
|---|---|---|
| DNA (ng/uL) (w/background) | 8.03 | 10.57 |
| DNA (ng/uL) (w/o background) | 7.30 | 9.75 |
| Extraction Volume | 5.6 | 5.2 |
| Total DNA Yield (ng) | 40.91 | 50.74 |

Figure 15:
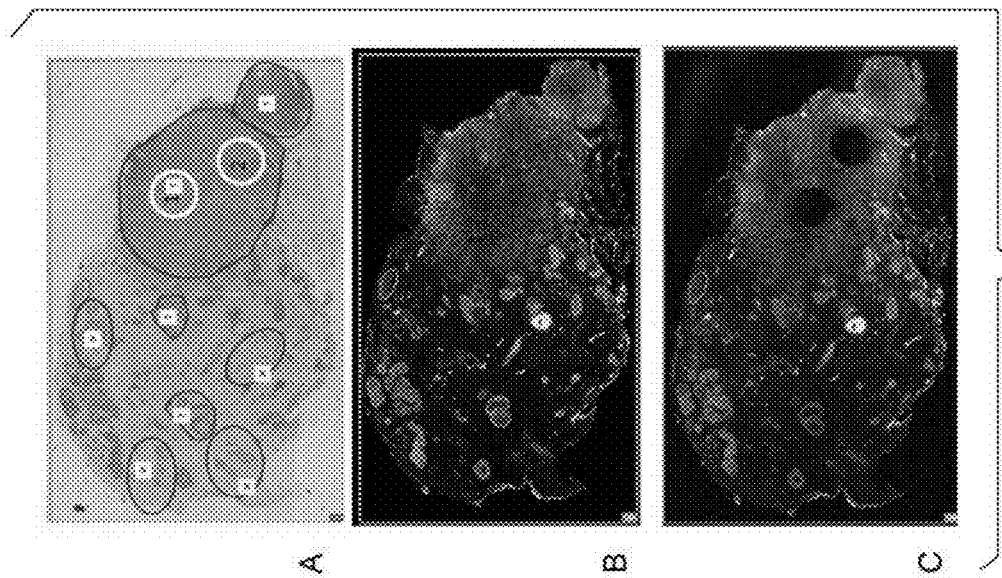
FIG. 15 is stained image of a breast invasive ductal carcinoma with the top panel showing DNA staining and including background, the middle panel showing staining with the background removed and the bottom panel after region of extraction removal.

The following is an example of an extraction performed with an extraction system, such as the systems disclosed herein. FIG. 15 shows images before and after extraction. Table 3 shows the extraction results:

TABLE 3

Extraction of Breast Invasive Ductal Carcinoma.

|  | Sample 1 | Sample 2 |
|---|---|---|
| DNA (ng/uL) (w/background) | 9.71 | 15.76 |
| DNA (ng/uL) (w/o background) | 8.65 | 14.27 |
| Extraction Volume | 5.4 | 5.2 |
| Total DNA Yield (ng) | 46.71 | 74.23 |

Technical effects of the invention include rapid isolation of regions of interest in a biological material without introducing a foreign material to the remainder of the sample and without wasting or damaging the remainder. The fluid delivery base as disclosed is configured to isolate a region of interest for extraction by self-aligning with other components of the system. Further, the extraction system provided herein provides isolation of the sample to prevent sample and/or caregiver contamination. By providing a platform for sealing a region of interest, liquefying the isolated contents of the region of interest, and recovering the liquefied material, the sample recovery is faster and more efficient relative to other techniques. In addition, the region of interest is isolated from other areas of the sample, preserving the remaining sample for further study.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of extracting material from a region of interest, comprising:
aligning one or more fluid channels of a fluid delivery base with an alignment member to define a region of interest on a sample, wherein the fluid delivery base and the alignment member are positioned on opposing surfaces of the sample such that the fluid delivery base and the alignment member are separated from one another by at least the sample and wherein the aligning comprises moving the fluid delivery base into a magnetic field of the alignment member, or moving a magnetic field of the fluid delivery base towards the alignment member;
delivering extraction fluid to the sample via the one or more fluid channels; and
collecting the extraction fluid via the one or more fluid channels.

2. The method of claim 1, comprising emitting light from the fluid delivery base onto the sample before aligning the one or more fluid channels.

3. The method of claim 2, wherein the light is emitted from a fiber optic light channel disposed within the one or more fluid channels.

4. The method of claim 1, comprising isolating the region of interest of the sample via a gasket, wherein the gasket is affixed to the fluid delivery base.

5. The method of claim 4, wherein the gasket contacts the sample.

6. A system for extracting material from a region of interest, comprising:
a fluid delivery base comprising one or more channels formed within the fluid delivery base, wherein the fluid delivery base comprises a magnet;
a gasket affixed to the fluid delivery base, wherein the gasket comprises at least one opening exposing an open end of at least one of the one or more channels;
a support comprising a sample-supporting surface configured to hold a sample against the gasket and an opposing surface; and
an alignment member coupled to the opposing surface in a fixed position and such that the support is positioned between the fluid delivery base and the alignment member, wherein the fluid delivery base is separable from the support and configured to move along a plane of the sample-supporting surface to align with the alignment member.

7. The system of claim 6, wherein the gasket comprises a plurality of openings, and wherein the one or more channels comprise a plurality of channels, wherein each gasket opening is coupled to at least one of the one or more channels.

8. The system of claim 7, wherein the plurality of channels are fluidically coupled to one another.

9. The system of claim 6, wherein the system is coupled to an extraction device comprising an imager, and wherein the extraction device is configured to:
acquire an image of a sample using image acquisition circuit;

designate the one or more regions of interest on the sample;

and align the fluid delivery base on the sample such that the gasket forms a seal about the one or more regions of interest.

10. The system of claim 6, wherein one or both of the alignment member or the fluid delivery base comprises a magnet and wherein a pull force of a magnetic field of one or both of the fluid delivery base or the alignment member reversibly holds the fluid delivery base on the support.

11. The system of claim 6, wherein one or both of the alignment member or the fluid delivery base are biased towards one another with a spring force.

12. The system of claim 6, wherein, in operation, the gasket contacts the sample.

13. The system of claim 6, wherein the gasket is configured to be removable from the fluid delivery base.

14. The system of claim 6, comprising an adaptor comprising one or more interior channels that couple to the one or more channels of the fluid delivery base.

15. The system of claim 6, wherein the gasket is positioned between the fluid delivery base and the sample-containing surface.

16. The system of claim 6, wherein the fluid delivery base and the alignment member, when in operation, align along an axis, wherein the axis intersects the at least one opening of the gasket.

17. The system of claim 6, wherein the one or more channels are substantially parallel to each other.

18. A system for extracting a material from a region of interest of a sample, comprising:

a fluid delivery base comprising a fluid inlet channel and a fluid outlet channel fluidically coupled to the fluid inlet channel, the fluid inlet channel arranged to deliver an extraction fluid to an isolated portion of the sample corresponds to the region of interest, for extracting the material from the region of interest, and the fluid outlet channel arranged to collect the extraction fluid and the material extracted from the same region of interest;

a gasket affixed to a sample-facing surface of the fluid delivery base, the gasket configured to isolate the region of interest upon direct contact with the sample;

a support comprising a sample-supporting surface configured to hold the sample against the gasket and an opposing surface; and an alignment member coupled to the opposing surface such that the support is positioned between the fluid delivery base and the alignment member, wherein the fluid delivery base is separable from the support and configured to align with the alignment member under magnetic force.

\* \* \* \* \*